United States Patent [19]

Eder et al.

[11] 4,066,674
[45] Jan. 3, 1978

[54] PROCESS FOR THE PREPARATION OF 1,3-OXYGENATED 8α-ESTRATRIENES AND NOVEL INTERMEDIATES OBTAINED THEREFROM

[75] Inventors: Ulrich Eder; Gerhard Sauer; Gregor Haffer; Guenter Neef; Rudolf Wiechert, all of Berlin, Germany

[73] Assignee: Schering Aktiengesellschaft, Berlin and Bergkamen, Germany

[21] Appl. No.: 741,497

[22] Filed: Nov. 12, 1976

[51] Int. Cl.² .............................................. C07J 1/00
[52] U.S. Cl. ................................................ 260/397.5
[58] Field of Search ..................................... 260/397.5

[56] References Cited

U.S. PATENT DOCUMENTS 3,951,959   4/1976   Prezewowsky et al. ......... 260/397.5

Primary Examiner—Elbert L. Roberts

Attorney, Agent, or Firm—Millen & White

[57] ABSTRACT

Novel 1,3-dialkoxy 8α-estratriene compounds of the formula

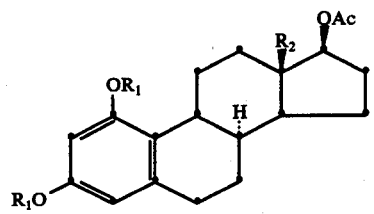

wherein $R_1$ is alkyl of 1–18 carbon atoms, $R_2$ is alkyl of 1–5 carbon atoms and Ac is alkanoyl of 1–8 carbon atoms, are obtained by a three-step synthesis from a tetrahydroindane-5-one compound.

11 Claims, No Drawings

PROCESS FOR THE PREPARATION OF 1,3-OXYGENATED 8α-ESTRATRIENES AND NOVEL INTERMEDIATES OBTAINED THEREFROM

BACKGROUND OF THE INVENTION

This invention relates to a process for the preparation of 1,3-oxygenated 8α-estratrienes of Formula I

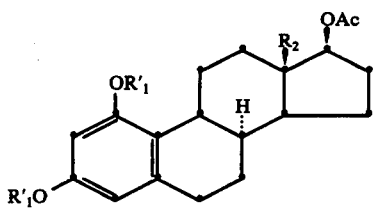

wherein $R_1'$ is alkyl or alkanoyl, $R_2$ is lower alkyl, and Ac is alkanoyl.

1,3-Oxygenated 8α-estratrienes of Formula I have a strongly vaginotropic effect with weakly uterotropic side effects and consequently are extremely suitable for the treatment of post-menopausal women. See DOS (German Unexamined Application) 2,336,431.

However, known commercial processes for the preparation of these compounds are very expensive.

The present invention provides a technically simpler process for production of these compounds, starting from readily accessible starting materials, and producing the desired compounds in a small number of synthetic steps, each having a good to very good yield.

SUMMARY OF THE INVENTION

In a compositional aspect, this invention relates to novel 1,3-oxygenated 8α-estratriene optical isomers of Formula Ia

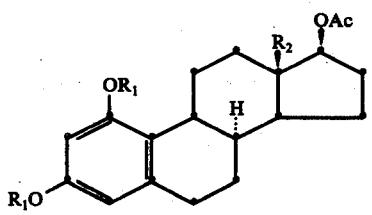

wherein $R_1$ is alkyl or aralkyl of up to 8 carbon atoms, $R_2$ is alkyl of 1–5 carbon atoms and Ac is alkanoyl of 1–8 carbon atoms.

This invention further relates to a process for the production of a 1,3-oxygenated 8α-estratriene of Formula Ia, by the steps of a. condensing, in the presence of a deprotonating agent, a compound of Formula II

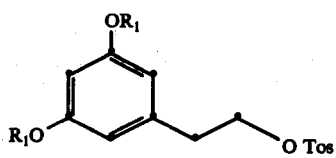

wherein $R_1$ is alkyl or aralkyl of up to 8 carbon atoms and Tos is tosylate, with a tetrahydro-indane-5-one compound of Formula III

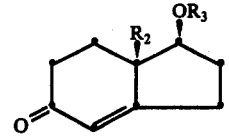

wherein $R_2$ is alkyl of 1–5 carbon atoms and $R_3$ is tert.-butyl, tetrahydropyranyl, tetrahydrofuranyl, α-ethoxyethyl, trimethylsilyl or tri-p-xylylsilyl, to produce a condensate of Formula IV

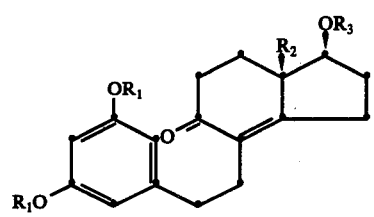

wherein $R_1$, $R_2$, and $R_3$ are as above;

b. cyclizing the condensate of Formula IV, in the presence of a strong acid and a carboxylic acid anhydride of 1–8 carbon atoms to an estrapentaene of Formula I

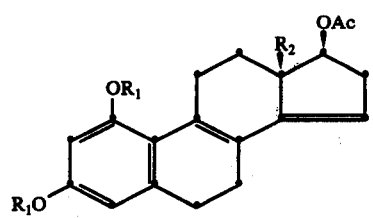

wherein $R_1$, $R_2$ and Ac are as above; and c. hydrogenating the estrapentaene of Formula V, in the presence of a hydrogenation catalyst, to the compounds of Formula Ia

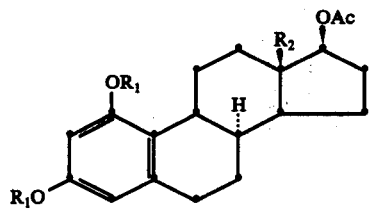

wherein $R_1$, $R_2$, and Ac are as above.

Optionally, alkoxy in the A-ring of compounds of Formula Ia are converted to alkanoyloxy of 1–8 carbon atoms in a further step.

DETAILED DESCRIPTION

Optically active starting compounds of Formula III can be synthesized by the simple method of DOS 2,014,757. Therefore, the process of this invention is especially well suited for production of optically active 1,3-oxygenated 8α-estratrienes.

$R_1$ and $R_1'$ alkyl and aralkyl groups are of 1–8 carbon atoms, for example, methyl, ethyl, butyl, tert.-butyl, hexyl, benzyl, phenethyl and octyl. Alkyl of 1–7 carbon atoms and aralkyl residues are preferred. Especially preferred are straight-chain alkyl of 1–2 carbon atoms, i.e., methyl and ethyl, and phenylalkyl, for example, benzyl.

$R_2$ are alkyl of 1-5 carbon atoms, e.g., methyl, ethyl, propyl, butyl, and pentyl. Methyl and ethyl are preferred.

$R_1'$ and Ac alkanoyl are residues of physiologically acceptable acids, preferably of organic carboxylic acids or 1-8 carbon atoms. Examples of such carboxylic acids are: formic acid, acetic acid, propionic acid, butyric acid, isobutyric acid, valeric acid, isovaleric acid, caproic acid, and enanthic acid. Particularly preferred alkanoyl are derived from acids of 1-3 carbon atoms, that is, formic acid, acetic acid, and propionic acid. Acetic acid is the most preferred.

Contemplated equivalents of alkanoyl of 1-8 carbon atoms include residues of aromatic acids, dicarboxylic acids and hydroxy acids, e.g., succinic acid, glutaric acid, adipic acid, benzoic acid, toluic acid, and lactic acid.

Compounds of Formula Ia include those wherein:
a. $R_1$ is methyl, ethyl or benzyl;
b. $R_2$ is methyl or ethyl, including (a); and
c. Ac is formyl, acetyl or propionyl, including (a) and (b).

$R_3$ are hydrocarbyl residues of readily cleavable ether blocking groups, for example, tert.-butyl, tetrahydropyranyl, tetrahydrofuranyl, α-ethoxyethyl, trimethylsilyl, and tri-p-xylylxilyl. tert.-Butyl and the tetrahydropyranyl are preferred.

Preferred deprotonating agents for the condensation step include alkali metal hydrides, alkali metal alcoholates and alkali metal amides. Examples of deprotonating agents are sodium hydride, sodium amide, potassium hydride, sodium tert.-butylate, lithium amide, and potassium triphenylmethyl. NaH is preferred.

The condensation reaction is conducted in an inert solvent, for example, polar ethers, such as 1,2-dimethoxyethane, 2',2'-dimethoxydiethyl ether, tetrahydrofuran, or dioxane; secondary or tertiary alcohols, e.g., isopropanol, 2-butanol, or tert.-butanol; or dipolar aprotic solvents, e.g., diemthylformamide, N-methylacetamide, N-methylpyrrolidone, and hexamethylphosphoric triamide. Mixtures of the above solvents and relatively non-polar solvents, e.g., benzene or toluene, can also be used.

Preferably, the condensation step is done at an elevated temperature from 30° C. to the boiling temperature of the solvent under an inert gas atmosphere, for example, argon or nitrogen.

Together with, or preferably after, addition of the deprotonating agent, the reaction mixture is treated with a tosylate of Formula II, preferably at a reaction temperature of +10° to 80° C.

High yields, 60-80%, of compounds of Formula IV are obtained. This is surprising to a person skilled in the art, because structurally analogous, mono-oxygenated tosylates can be condensed to compounds of Formula III only in moderate yields. See U.S. Pat. No. 3,317,566.

Cyclization of compounds of Formula IV is preferably conducted in an inert gas atmosphere, e.g., under nitrogen or argon atmosphere, in the presence of a strong acid, for example, mineral acids, sulfonic acids, Lewis acids, and strongly dissociated carboxylic acids. Examples of these acids are: formic, monofluoroacetic acid, trichloroacetic acid, oxalic acid, malonic acid, hydrogen chloride, sulfuric acid, phosphoric acid, perchloric acid, methanesulfonic acid, benzenesulfonic acid, p-toluenesulfonic acid, and boron trifluoride.

Mineral acids, for example, perchloric acid and phosphoric acid, are preferred.

Protonic solvents suitable for the cyclization include carboxylic acids, e.g., formic acid, acetic acid, and propionic acid; and dipolar aprotic solvents, e.g., dimethylformamide, N-methylpyrrolidone, and hexamethylphosphoric triamide.

The cyclization can be effected at low temperatures, for example, 0° C., or at an elevated temperature of up to about 150° C. Preferably, the reaction temperature is 5°-25° C.

The acyl anhydrides used in the reaction mixture are, for example, anhydrides of fatty acids of 1-8 carbon atoms and mixed anhydrides. Preferred anhydrides are formyl acetate, acetic anhydride, and propionic anhydride.

It is surprising to those skilled in the art that, in this reaction step, cyclization and cleavage of the etherified hydroxy group on the C-17 atom occur at the same time, along with simultaneous esterification. Thus, a simplified synthetic procedure has been discovered, by which the desired product can be obtained in good yields without expensive separation operations.

Compounds of Formula V are hydrogenated catalytically. Suitable catalysts include, inter alia, heavy metal catalysts, preferably those of subgroup VIII, e.g., palladium, optionally distributed on a support, such as calcium carbonate, activated charcoal, or barium sulfate; and Raney nickel.

The hydrogenation can be conducted at room temperature or a lower or higher temperature. A temperature of 0° to 50° C. is generally selected for the reaction.

The hydrogenation can be effected under normal pressure or elevated pressure. Preferably a hydrogen pressure of 1-80 atmospheres is used.

In a most preferred embodiment, the method of this invention is that wherein the deprotonating agent of step (a) is NaH; $R_3$ in the tetrahydroindane-5-one is tert.-butyl or tetrahydropyranyl; the strong mineral acid for cyclizing said condensate of step (a) is perchloric or phosphoric acid; and cyclization of said condensate of step (a) is done in a mixture containing formyl acetate, acetic anhydride or propionic anhydride.

Conversion of alkoxy present on the A-ring to an alkanoyloxy is accomplished in accordance by known methods. For example, cleavage with a hydrohalic acid in the presence of a lower carboxylic acid at a temperature below 150° C. is followed by acylation in the 1,3-position, using pyridine/acid anhydride or pyridine/acid chloride at room temperature. The starting compounds are prepared as follows:

Methyl Ester of 3,5-Dimethoxyphenylacetic Acid

Under agitation, 522.5 g. (3 moles) of the dimethyl ester of acetonedicarboxylic acid is mixed in incremental portions with 5.3 g. of metallic sodium. After 20 hours at room temperature, the mixture is heated for 2 hours to an internal temperature of 140° C., whereby the volatile components are distilled off. The still warm residue (~ 100° C.) is combined with 2.82 liters of 12% aqueous sodium hydroxide solution; the mixture is then heated for 2 hours to 100° C., and again volatile components (methanol) are removed by distillation. The solution, cooled to 80° C., is then combined dropwise with 245 ml. of concentrated sulfuric acid, refluxed for 3 hours, cooled, and, after saturation with NaCl, extracted with ethyl acetate.

The extracts are washed out repeatedly with semisaturated NaCl solution, dried with $Na_2SO_4$, and filtered. After the solvent has been distilled off under vacuum, there remains 182.9 g. of crude 3,5-hydroxyphenylacetic acid as a semicrystalline product.

Within 40 minutes, a solution of 182.9 g. of crude 3,5-hydroxyphenylacetic acid and 315 ml. of dimethyl sulfate in 800 ml. of acetone is added dropwise with vigorous agitation to a boiling suspension of 470 g. of potassium carbonate in 1600 ml. of acetone. The reaction mixture is then refluxed for 16 hours. The cooled suspension is filtered. The residue on the filter is washed repeatedly with acetone. The filtrates are combined and the solvent is distilled off under vacuum.

The brownish yellow crude product (188.7 g.) is distilled off under a high vacuum.

Yield: 154.2 g. (49% of theory) of the methyl ester of 3,5-dimethoxyphenylacetic acid as a colorless oil, b.p. 110°–115° C./0.03 torr.

3,5-Dimethoxyphenethyl Alcohol

Within 40 minutes, 1.12 liters of a 20% solution of diisobutylaluminum hydride in toluene is added dropwise to a solution, cooled to −40° C., of 132.3 g. of the methyl ester of 3,5-dimethoxyphenylacetic acid in 1.3 l. of absolute toluene, the temperature rising to −10° C. during this step. After another 20 minutes at −10° C., 151 ml. of water is carefully added dropwise so that the temperature does not exceed +10° C. 200 g. of sodium sulfate is then added to the reaction mixture, and the latter is stirred for 2 hours at room temperature. The solids are filtered off and a subsequent washing step is performed with a total of 1 liter of methylene chloride.

The solvent is distilled off under vacuum from the combined filtrates, thus obtaining 108.1 g. (94.4% of theory) of crude 3,5-dimethoxyphenethyl alcohol which is utilized in the subsequent stage without any further purification.

(3,5-Dimethoxyphenethyl) Ester of p-Toluenesulfonic Acid

Within 40 minutes, a solution of 150 g. of p-toluenesulfochloride in 330 ml. of pyridine is added dropwise to a solution, cooled to 0° C., of 109.9 g. of crude 3,5-dimethoxyphenethyl alcohol in 330 ml. of pyridine. After maintaining the reaction mixture under ice cooling for 2 hours and at room temperature for 2 hours, the suspension is stirred into 5 l. of icecold 1.5N HCl and extracted with methylene chloride. The extracts are washed neutral twice with semisaturated $NaHCO_3$ solution and then with dilute NaCl solution. After drying over $Na_2SO_4$, the solvent is distilled off under vacuum, and the residue (∼200 g.) is crystallized from ether.

Yield: 135.4 g. (62.1% of theory) of the (3,5-dimethoxyphenethyl) ester of p-toluenesulfonic acid, m.p. 73°–75° C.

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in anyway whatsoever.

EXAMPLE 1

First Stage (1S,7aS)-1-tert.-Butoxy-7a-methyl-4-(3,5-dimethoxyphenethyl)-5,6,7,7a-tetrahydroindan-5-one A degassed solution of 75 g. of (1S,7aS)-1-tert.-butoxy-7a-methyl-5,6,7,7a-tetrahydroindan-5-one-(+) in 750 ml. of absolute tetrahydrofuran, under argon, is combined with 9.74 g. of NaH (freed from oil with hexane) and refluxed for 20 hours. At 40°–45° C., a solution of 125 g. of the 3,5-dimethoxyphenethyl ester of p-toluenesulfonic acid in 375 ml. of absolute tetrahydrofuran is then added dropwise thereto within 20 minutes. After a reaction time of 20 hours at 40°–45° C., 300 ml. of saturated sodium hydrogen phosphate solution is added to the reaction mixture. The solvent is distilled off under vacuum and the residue is extracted with a total of 2 l. of methylene chloride. After the mixture has been washed neutral, dried with sodium sulfate, and the solvent has been distilled off under vacuum, there remains 146.6 g. of a brown, oil crude product.

Second Stage

17β-Acetoxy-1,3-dimethoxy-1,3,5(10),8,14-estrapentaene

A solution of 146.6 g. of crude (1S,7aS)-1-tert.-butoxy-7a-methyl-4-(3,5-dimethoxyphenethyl)-5,6,7,7a-tetrahydroindan-5-one in 375 ml. of glacial acetic acid and 87 ml. of acetic anhydride is combined under a protective argon gas atmosphere with cooling with 3.6 ml. of 72% aqueous perchloric acid. After another hour with cooling (10°–15° C.), the mixture is agitated for 30 hours at room temperature, and the dark-brown reaction solution is then stirred into 3 l. of ice water. During this step, the product is already partially precipitated in crystalline form. The product is then extracted repeatedly with toluene. The toluene extracts are washed with semisaturated $NaHCO_3$ solution and then with water until neutrality has been attained, whereafter the product is dried with sodium sulfate and the solvent is distilled off under vacuum. The crystalline crude product is chromatographed on silica gel with hexane-acetone (0–15%). The fractions, which are uniform as determined by thin-layer chromatography, are combined and dried under a high vacuum.

Yield: 67.19 g. (56% of theory); m.p. 142.5°–143.5° C. (diisopropyl ether).

Third Stage

17β-Acetoxy-1,3-dimethoxy-8α-estra-1,3,5(10)-triene 18.85 g. of 17β-acetoxy-1,3-dimethoxy-1,3,5(10),8,14-estrapentaene is hydrogenated in 400 ml. of tolune with 5 g. of anhydrous Raney nickel. The rection time at room temperature and under a pressure of 50 atmospheres hydrogen is 16 hours.

Yield: 14.8 g. (78.5% of theory); m.p. 109°–110° C. (methanol).

Fourth Stage 1,3,17β-Triacetoxy-8α-estra-1,3,5(10)-triene

A solution of 9 g. of 17β-acetoxy-1,3-dimethoxy-8α-estra-1,3,5(10)-triene in 99 ml. of HBr, glacial acetic acid (37%), and 27 ml. of water is heated on a steam bath for 6 hours, then cooled, stirred into ice water - NaCl, and extracted with methylene chloride. The $CH_2Cl_2$ extracts are washed repeatedly with semisaturated NaCl solution, dried with Na$_2$SO$_4$, and the solvent is distilled off under vacuum. The residue is combined with 185 ml. of pyridine and 80 ml. of acetic anhydride and allowed to stand for 16 hours at room temperature. After stirring the mixture into an ice water — NaCl mixture, the mixture is worked up as usual.

The crude product is chromatographed on silica gel with petroleum ether — acetone (10-30%).

Yield: 7.67 g.; m.p. 156°-157° C. (isopropyl ether).

The preceding examples can be repeated with similar success by substituting the generically and specifically described reactants and/or operating conditions of this invention for those used in the preceding examples.

From the foregoing description, one skilled in the art can easily ascertain the essential characteristics of this invention, and without departing from the spirit and scope thereof, can make various changes and modifications of the invention to adapt it to various usages and conditions.

What is claimed is:

1. A process for the production of a 1,3-oxygenated-8α-estratriene optical isomer of the formula

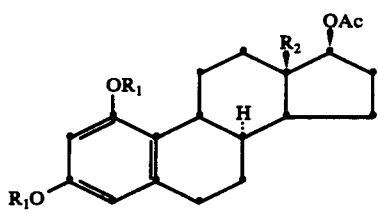

wherein $R_1$ is alkyl or aralkyl of up to 8 carbon atoms, $R_2$ is alkyl of 1-5 carbon atoms and Ac is alkanoyl of 1-8 carbon atoms, which comprises the steps of:

a. condensing, in the presence of a deprotonating agent, a compound of the formula

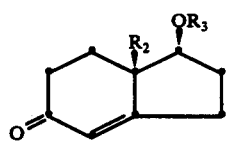

wherein $R_1$ is alkyl or aralkyl of up to 8 carbon atoms and Tos is tosyloxy, with a tetrahydroindane-5-one compound of the formula

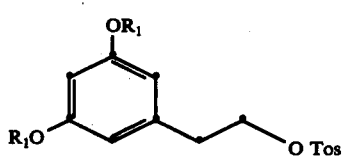

wherein $R_2$ is alkyl of 1-5 carbon atoms and $R_3$ is tert.-butyl, tetrahydropyranyl, tetrahydrofuranyl, α-ethoxyethyl, trimethylsilyl or tri-p-xylylsilyl, to produce a condensate of the formula

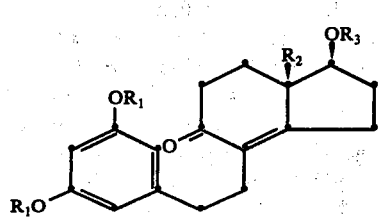

wherein $R_1$, $R_2$, and $R_3$ are as above;

b. cyclizing the condensate in the presence of a strong acid and a carboxylic acid of 1-8 carbon atoms to an estrapentaene of the formula

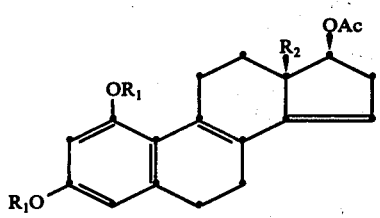

wherein $R_1$, $R_2$, and Ac are as above; and c. hydrogenating the estrapentaene in the presence of a hydrogenation catalyst to said 1,3-oxygenated-8α-estratriene.

2. The method of claim 1, comprising the further step of converting the $R_1$ groups of the thus-produced 1,3-oxygenated-8α-estratriene to alkanoyl of 1-8 carbon atoms.

3. The method of claim 1, wherein the deprotonating agent of step (a) is NaH.

4. The method of claim 1, wherein $R_3$ in the tetrahydroindane-5-one compound is tert.-butyl or tetrahydropyranyl.

5. The method of claim 1, wherein the strong acid for cyclizing said condensate of step (a) is perchloric or phosphoric acid.

6. The method of claim 1, wherein cyclization of said condensate of step (a) is done in a mixture containing formyl acetate, acetic anhydride or propionic anhydride.

7. The method of claim 1, wherein the deprotonating agent of step (a) is NaH; $R_3$ is the tetrahydroindane-5-one is tert.-butyl or tetrahydropyranyl; the strong mineral acid for cyclizing said condensate of step (a) is perchloric or phosphoric acid; and cyclization of said condensate of step (a) is done in a mixture containing formyl acetate, acetic anhydride or propionic anhydride.

8. The method of claim 1 wherein the deprotonating agent in step (a) is an alkali metal hydride, alkali metal alcoholate or alkali metal amide; wherein in step (b) the strong acid is a mineral acid, a sulfonic acid, a Lewis acid or a strongly dissociated carboxylic acid, and the cyclization is conducted in a protonic solvent; wherein in step (c) the hydrogenation catalyst is a heavy metal catalyst of subgroup VIII of the Periodic Table or Raney nickel.

9. The method of claim 8 wherein condensation step (a) is conducted under an inert atmosphere and in an inert solvent at from 30° C. to the boiling temperature of the solvent; wherein cyclization step (b) is conducted in an inert atmosphere in the presence of a mineral acid; and hydrogenation step (c) is conducted employing Raney nickel as the hydrogenation catalyst.

10. The method of claim 9 wherein in step (a) the deprotonating agent is NaH, $R_3$ is tert.-butyl or tetrahydropyranyl and the strong acid is perchloric or phosphoric acid; and step (b) is conducted in the presence of formyl acetate, acetic anhydride or propionic anhydride.

11. The method of claim 1 wherein in step (a), $R_1$ and $R_2$ are methyl or ethyl, $R_3$ is tert.-butyl or tetrahydropyranyl and the deprotonating agent is NaH.

* * * * *